US00PP11565P

United States Patent [19]

Lemon

[11] Patent Number: Plant 11,565

[45] Date of Patent: Oct. 10, 2000

[54] VARIETY OF GERANIUM NAMED 'PATRIOT VIOLET'

[75] Inventor: David G. Lemon, Lompoc, Calif.

[73] Assignee: Oglevee, Ltd., Connellsville, Pa.

[21] Appl. No.: 09/162,687

[22] Filed: Sep. 29, 1998

[51] Int. Cl.[7] ..... A01H 5/00

[52] U.S. Cl. ..... Plt./329

[58] Field of Search ..... Plt./329, 330, 325, Plt./324, 328

[56] References Cited

U.S. PATENT DOCUMENTS

P.P. 7,085 12/1989 Hofmann ..... Plt./329
P.P. 8,286 6/1993 Trees ..... Plt./329

*Primary Examiner*—Howard J. Locker
*Assistant Examiner*—Michelle Kizilkaya
*Attorney, Agent, or Firm*—Web Ziesenheim Logsdon Orkin & Hanson, P.C.

[57] ABSTRACT

A new and distinct zonal geranium plant with deep violet flowers above medium green foliage having slight zoning. The new variety excels in various weather conditions and has an improved plant habit, flower form and outdoor performance over 'Americana Violet'.

1 Drawing Sheet

BACKGROUND OF THE INVENTION

This discovery is a new and distinct variety of geranium plant identified by the varietal name of 'Patriot Violet', Breeder No. 4DG863 and Oglevee, Ltd. No. 5077. The seedling of the present variety was discovered by David G. Lemon in a selected breeding program in Connellsville, Pa. The new variety is a selection from the crossing of the commercial variety 'Americana Violet', U.S. Plant Pat. No. 8,750, and the commercial variety 'BSR-194 Cherry', U.S. Plant Pat. No. 8,286. The new variety was first asexually reproduced by cuttings on Aug. 14, 1995 in Connellsville, Pa. It has been found to retain its distinctive characteristics through successive propagations.

The new variety, when grown in a glass greenhouse in Connellsville, Pa. using full light, 60° F. night temperature, 68° F. day temperature and grown in a soilless media with constant fertilizer at 200–250 ppm nitrogen and potassium, has a response time from a rooted cutting to a flowering plant in a 10 inch pot of six weeks.

DESCRIPTION OF THE DRAWING

The accompanying phtographic drawing illustrates the new variety, with the color being as nearly true as is possible with color illustrations of this type.

DESCRIPTION OF THE PLANT

The following detailed description set forth the characteristics of the new variety. The data which define these characteristics were collected from asexual reproductions carried out at Oglevee, Ltd., 152 Oglevee Lane, Connellsville, Pa. 15425. The color readings on a plant grown in a 10 inch pot were taken indoors under 200–220 foot candles of cool white fluorescent light. Color references are primarily to the R.H.S. Colour Chart of The Royal Horticultural Society of London.

THE PLANT

Classification:
- *Botanical.*—*Pelargonium×hortorum.*
- *Varietal.*—Florists' zonal geranium named 'Patriot Violet'.

Form: Uniform, medium mound.
Height: 17.0 cm from media in a 10 cm pot.

Growth: Strong basal branching.
Strength: Needs no artificial support.
Foliage: Stalked leaf attachment.
Leaves:
- *Size.*—7.3–10.0 cm across.
- *Shape.*—Reniform, cordate base.
- *Margin.*—Crenate.
- *Texture.*—Smooth, pubescent.
- *Color.*—Top: Green Group 137C. Bottom: Green Group 138B. Zone: Present but not prominent; Green Group 137A.
- *Ribs and veins.*—Venation: Palmate. Color: Yellow-Green Group 146D.

Petioles:
- *Length.*—5.5–8.0 cm.
- *Color.*—Yellow-Green Group 146B.

Stem:
- *Color.*—Yellow-Green Group 146C.
- *Internode length.*—2.0–3.8 cm.

THE BUD

Shape: The bud shape is an elliptical cluster. The bud shape is determined before the buds are showing color and the peduncle is not fully developed. The numer of buds per cluster is taken when some color can be seen or when the florets are fully open. The variety has 28–44 buds/florets per cluster.
Size: 3.0–3.4 cm across when just showing color.

INFLORESCENCE

Blooming habit: Continuous, semi-double; free flowering.
Borne: Umbel, floret on pedicel, pedicel on peduncle.
Closed florets:
- *Bud size.*—0.9–1.3 cm long when just showing color.

Open Florets:
- *Form.*—Flat to slightly cupped.
- *Size of fully open bloom.*—Umbel: 8.5–10.0 cm across. Floret: 4.5–5.5 cm across.
- *Color.*—Top: Upper Two petals: Red-Purple Group 61A at outer edge blending to Red-Purple Group 61B towards the middle. Veining of Red Group 46A. Base of petal is white but can only be seen when petals are removed. Lower petals: Red-Purple Group 61A at the edge blending to Red-Purple Group 61B towards the middle with veining of Red-Purple Group 64A. Bottom: Red-Purple Group 61lB with white base and veins showing through. Eye: Red-Purple Group 41A with veins of Red Group 46A running therethrough. Petals: 7–8 in number.

Texture and appearance: Reflective, velvety, smooth; appears from a distance as flowers of bright deep violet with contrasting red orange area present on some petals over medium green foliage with slightly darker zone.

Petaloids:

*Quantity.*—2–3.

*Shape.*—Twisted, irregular.

*Color.*—Top: Red-Purple Group 61A. Bottom: Red-Purple Group 61B.

Pedicel:

*Length.*—2.7–3.3 cm.

*Color.*—Yellow-Green Group 146C with Greyed-Red Group 180A.

Peduncle:

*Length.*—17.0–18.0 cm.

*Color.*—Yellow-Green Group 146B.

Disease resistance: Not known.

Lasting quality: Holds large flowers on strong stems; flowers last about 7–14 days.

REPRODUCTIVE ORGANS

Stamens:

*Anthers.*—2–3 mm long.

*Filaments.*—7–9 mm long; white with pink tips.

*Pollen color.*—Golden brown.

Pistils:

*Number.*—1; five parted.

*Length.*—8–9 mm.

*Stigma color.*—Red-Purple Group 60C.

*Style.*—2–3 mm long.

*Ovaries.*—Pale green; superior; 6.0 mm long.

Fruit: None observed.

GENERAL CHARACTERISTICS

The vibrant violet color of 'Patriot Violet' is similar to 'Americana Violet' but with improved plant habit, flower form and outdoor performance. The new variety has been trialed both indoors and outdoors since 1995 and compared to 'Americana Violet' it has excelled in a variety of weather conditions.

I claim:

1. A new and distinct variety of geranium plant named 'Patriot Violet' as described and illustrated herein.

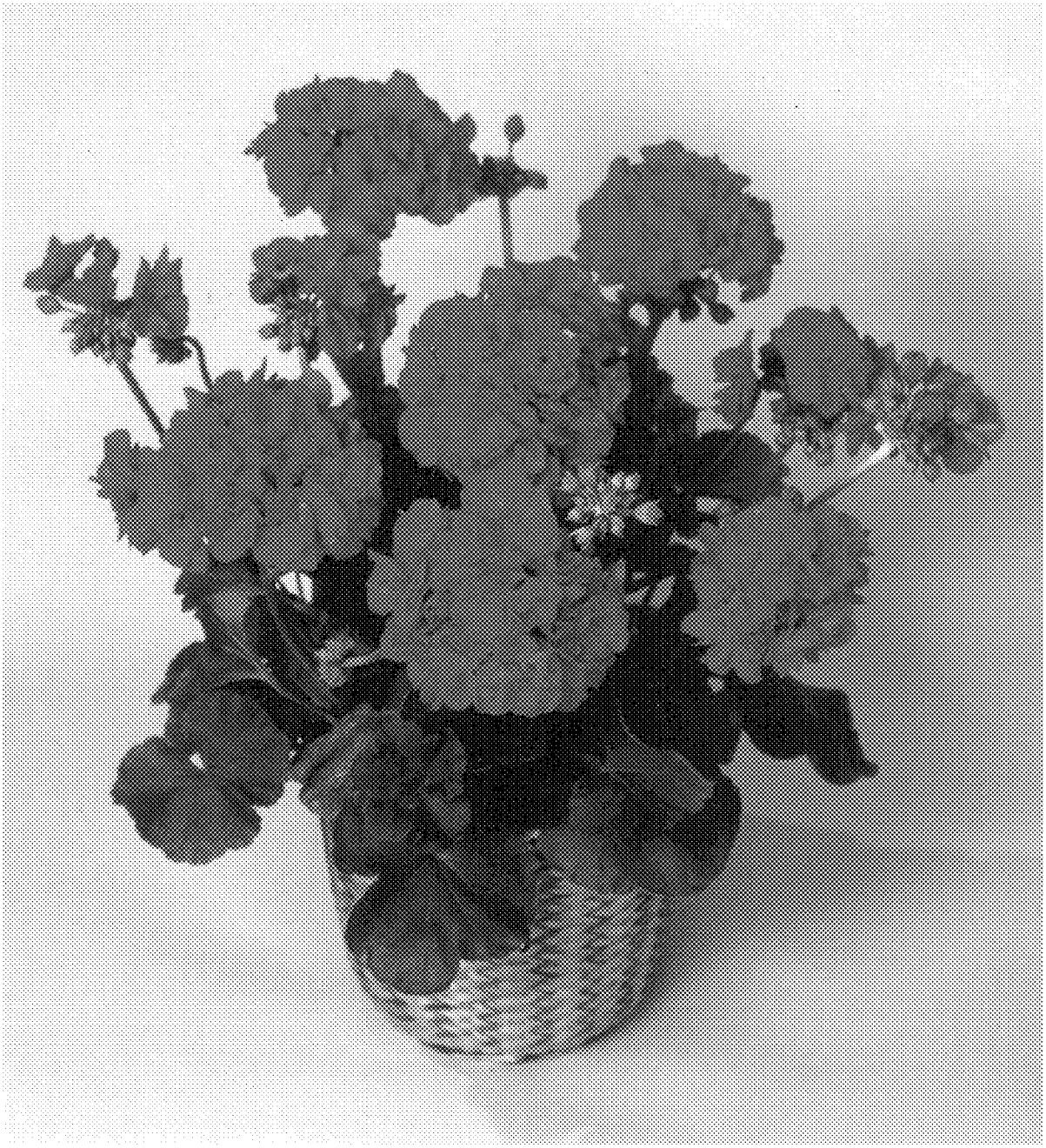

* * * * *